US012121454B2

(12) United States Patent
Cordaro

(10) Patent No.: US 12,121,454 B2
(45) Date of Patent: Oct. 22, 2024

(54) ADDITIVE MANUFACTURED TITANIUM BONE DEVICE

(71) Applicant: HT Medical, LLC, Tulsa, OK (US)

(72) Inventor: Nicholas Michael Cordaro, Vista, CA (US)

(73) Assignee: HT Medical, LLC, Tulsa, OK (US)

( * ) Notice: Subject to any disclaimer, the term of this patent is extended or adjusted under 35 U.S.C. 154(b) by 332 days.

(21) Appl. No.: 17/157,322

(22) Filed: Jan. 25, 2021

(65) Prior Publication Data

US 2021/0307910 A1    Oct. 7, 2021

Related U.S. Application Data

(63) Continuation of application No. 15/519,450, filed as application No. PCT/US2015/055400 on Oct. 13, 2015, now Pat. No. 10,898,333.

(Continued)

(51) Int. Cl.
*A61F 2/44* (2006.01)
*A61B 50/30* (2016.01)
*A61F 2/30* (2006.01)
*B33Y 80/00* (2015.01)
*B22F 3/11* (2006.01)
(Continued)

(52) U.S. Cl.
CPC ............ *A61F 2/4455* (2013.01); *A61B 50/30* (2016.02); *A61F 2/30* (2013.01); *A61F 2/30942* (2013.01); *A61F 2/44* (2013.01); *A61F 2/442* (2013.01); *A61F 2/447* (2013.01); *B33Y 80/00* (2014.12); *A61F 2002/30143* (2013.01); *A61F 2002/30263* (2013.01); *A61F 2002/30593* (2013.01); *A61F 2002/30785* (2013.01); *A61F 2002/30789* (2013.01); *A61F 2002/3092* (2013.01); *A61F 2002/30952* (2013.01); *A61F 2002/30968* (2013.01); *A61F 2002/3097* (2013.01); *A61F 2002/30985* (2013.01); *A61F 2310/00023* (2013.01); *B22F 3/11* (2013.01); *B22F 10/12* (2021.01); *B22F 10/14* (2021.01);
(Continued)

(58) Field of Classification Search
CPC ............ A61F 2/44; A61F 2/442; A61F 2/447; A61F 2/30; A61F 2/30942; A61B 50/30
See application file for complete search history.

(56) References Cited

U.S. PATENT DOCUMENTS

| 9,039,766 | B1 * | 5/2015 | Fonte | A61F 2/3094 |
| | | | | 623/17.13 |
| 10,898,333 | B2 * | 1/2021 | Cordaro | A61F 2/447 |
| 2005/0112397 | A1 * | 5/2005 | Rolfe | A61F 2/4455 |
| | | | | 606/76 |
| 2006/0217806 | A1 * | 9/2006 | Peterman | A61F 2/447 |
| | | | | 606/90 |

(Continued)

*Primary Examiner* — Christopher J Beccia
(74) *Attorney, Agent, or Firm* — David Meibos; Maywood IP Law

(57) ABSTRACT

Disclosed herein is an orthopedic implant device comprising a porous structure, approximating the shape of a bone, and having modulus of elasticity similar to that of said bone. In one embodiment, further disclosed herein is a method of treating injuries or diseases affecting bones or muscles comprising providing an orthopedic implant device, wherein the orthopedic implant device comprising a porous structure, approximating the shape of a bone, and having a modulus of elasticity similar to that of bone, and using the orthopedic implant device to treat injuries and diseases affecting bones and muscles in a mammal. In another embodiment, disclosed herein is a method of manufacturing an orthopedic implant device using an additive manufacturing (AM) method.

35 Claims, 21 Drawing Sheets

Related U.S. Application Data

(60) Provisional application No. 62/064,888, filed on Oct. 16, 2014.

(51) Int. Cl.
*B22F 10/12* (2021.01)
*B22F 10/14* (2021.01)
*B22F 10/18* (2021.01)
*B22F 10/28* (2021.01)
*B22F 10/66* (2021.01)
*B33Y 10/00* (2015.01)

(52) U.S. Cl.
CPC .............. *B22F 10/18* (2021.01); *B22F 10/28* (2021.01); *B22F 10/66* (2021.01); *B33Y 10/00* (2014.12)

(56) References Cited

U.S. PATENT DOCUMENTS

| | | | | |
|---|---|---|---|---|
| 2007/0142914 | A1* | 6/2007 | Jones | A61L 27/56 623/14.13 |
| 2010/0137990 | A1* | 6/2010 | Apatsidis | A61F 2/4425 606/301 |
| 2011/0014081 | A1* | 1/2011 | Jones | C23C 24/10 419/2 |
| 2012/0191200 | A1* | 7/2012 | Choren | A61F 2/3094 623/18.11 |
| 2012/0312778 | A1* | 12/2012 | Ullrich, Jr. | C23C 14/34 451/28 |
| 2013/0116793 | A1* | 5/2013 | Kloss | A61F 2/442 623/17.16 |
| 2014/0025181 | A1* | 1/2014 | Vanasse | B33Y 50/00 219/76.1 |
| 2014/0121777 | A1* | 5/2014 | Rosen | A61F 2/4455 623/17.16 |

* cited by examiner

ADDITIVE MANUFACTURED TITANIUM BONE DEVICE

CROSS REFERENCE TO RELATED APPLICATIONS

This application is a continuation of U.S. application Ser. No. 15/519,450, filed on Apr. 14, 2017, which is a § 371 National Stage filing of PCT/US2015/055400 filed on Oct. 13, 2015, titled ADDITIVE MANUFACTURED TITANIUM BONE DEVICE, which claims the benefit and priority of U.S. Provisional Application Ser. No. 62/064,888, filed Oct. 16, 2014, all of which are hereby incorporated by reference herein in their entireties, including all references and appendices cited therein for all purposes.

FIELD OF THE INVENTION

The present disclosure is in the medical and biomedical field, specifically orthopedic applications.

BACKGROUND OF THE DISCLOSURE

Orthopedic implants are well known in the art. Common orthopedic implants are associated with, for example, the spine, spinal articulations, intervertebral discs, facet joints, shoulder joints, knee, hip and shoulder, elbows, wrists, hands, finger joints, ankles, wrists, feet and toe joints.

Clinical reports of more modernized titanium interbody fusion devices, cages, have demonstrated low subsidence as compared to earlier titanium interbodies. Upon closer examination of the historical and modernized titanium interbodies, a large discrepancy in surface contact area to the endplates can be noted. The smaller contact surface of presently available implant devices to the endplates result in increased adjacent bone surface area pressure, which in turn caused mechanical subsidence of the device. The subsidence issue was partially solved by plastic interbodies, such as Polyetheretherketone (PEEK) or PEAK. Currently available plastic interbodies have thicker walls, required to produce appropriate device strength characteristics. This also gives the plastic devices an increased surface contact area, reducing the surface pressure and likely playing a key role in limiting clinical subsidence. However, thinner walls are preferred to allow for increased bone graft volume.

Thus there exists a need for a new orthopedic device that prevents subsidence, while at the same time, allows for easy and increased bone grafting.

SUMMARY OF THE DISCLOSURE

Various embodiments include an orthopedic implant device, comprising a porous structure that approximates the shape of a bone, and has a modulus of elasticity similar to that of said bone. In another embodiment, manufacturing the device comprises additive manufacturing (AM). In another embodiment, the porous structure has a porosity of 15% to 65%. In another embodiment, the porous structure has a porosity of 25-35%. In another embodiment, the modulus of elasticity is less than 50 GPa. In another embodiment, the orthopedic implant device is made of titanium or titanium alloy. In another embodiment, the porous structure is simple cubic, face centered cubic, body centered cubic, or hexagonal close packed structure. In another embodiment, the implant is an interbody fusion device. In another embodiment, the implant has a large surface contact area to the endplates to prevent linear subsidence while carrying a sufficiently large volume of bone graft area within the device to fuel the natural occurrence of a fusion. In another embodiment, the implant has large internal voids for bone graft. In another embodiment, the cross sectional area as related to the thickness within the device is less than 90% of that of the endplates. In another embodiment, the thickness within the device is 25% to 50% of that of the endplates. In another embodiment, the thin walls enable increased bone graft. In another embodiment, the device has a variable entry angle. In another embodiment, the variable entry angle maximizes the contact surface area to the vertebral body. In another embodiment, the entry angle is gradually decreased to offset the increasing insertion force. In another embodiment, the implant may be incorporated into expandable interbody cages, plates, screws, or other orthopedic devices benefitting from additive manufacturing. In another embodiment, the device is sterile packed using HA-nano Surface technology. In another embodiment, the device is described in FIGS. 32-39 herein. In another embodiment, the device is made of titanium.

Other embodiments include a method of treatment, comprising providing an orthopedic device comprising a porous structure that approximates the shape of a bone and has modulus of elasticity similar to that of said bone, and treating a disease and/or injury by implanting the orthopedic device in a mammal. In another embodiment, the disease is osteoporosis, Paget's disease, osteogeneis imperfecta, bone cancer, rickets, osteomalacia, acromegaly, Perthes' disease, fibrous dysplasia, or oteromyelitis. In another embodiment, the mammal is human. In another embodiment, the mammal is an animal. In another embodiment, treating comprises healing. In another embodiment, treating comprises strengthening. In another embodiment, treating comprises straightening. In another embodiment, the orthopedic device is inserted adjacent to a bone structure. In another embodiment, the orthopedic device is inserted inside a bone structure. In another embodiment, the orthopedic device is an intervertebral interbody. In another embodiment, the intervertebral interbody has a variable entry angle to first maximize the contact surface area to the vertebral body, and the entry angle is gradually decreased to offset the increasing insertion force. In another embodiment, the orthopedic device is inserted diagonally across the interbody space relative to the sagittal and coronal planes. In another embodiment, the orthopedic device couples two adjacent vertebrae. In another embodiment, the orthopedic device facilitates motion between the two adjacent vertebrae. In another embodiment, the orthopedic device is described in FIGS. 32-39 herein. In another embodiment, the orthopedic device is manufactured using Additive Manufacturing (AM). In another embodiment, the orthopedic device is manufactured using a series of steps of subsequently laser melting thin metal layers to create complex geometries. In another embodiment, the orthopedic device is manufactured using lost-wax casting, investment casting, or die casting with fillers. In another embodiment, the orthopedic device comprises titanium.

Other embodiments include a method of manufacturing an orthopedic implant device, comprising inputting a 3-dimensional model to an additive manufacturing device, and using the additive manufacturing device to manufacture the orthopedic implant device. In another embodiment, the orthopedic implant device comprises a porous structure that approximates the shape of a bone and has a modulus of elasticity similar to that of said bone. In another embodiment, the 3-dimensional model is created with computer aided design package. In another embodiment, the 3-dimensional model is created using a 3-dimensional scanner. In another embodiment, the 3-dimensional model is created using a digital camera and photogrammetry software. In another embodiment, the porous structure has a porosity of 15% to 65%. In another embodiment, the porous structure has a porosity of 25-35%. In another embodiment, the modulus of elasticity is less than 50 GPa. In another embodiment, the orthopedic implant device is made of titanium or titanium alloy. In another embodiment, the porous structure is simple cubic, face centered cubic, body centered cubic, or hexagonal close packed structure. In another embodiment, the orthopedic implant device is an interbody fusion device. In another embodiment, the orthopedic implant device has a large surface contact area to the endplates to prevent linear subsidence while carrying a sufficiently large volume of bone graft area within the device to fuel the natural occurrence of a fusion. In another embodiment, the orthopedic implant device has internal voids for bone graft. In another embodiment, the orthopedic implant device has a variable entry angle. In another embodiment, the variable entry angle maximizes the contact surface area to the vertebral body. In another embodiment, the entry angle is gradually decreased to offset the increasing insertion force. In another embodiment, the orthopedic implant device is incorporated into expandable interbody cages, plates, screws, or other orthopedic devices benefitting from additive manufacturing. In another embodiment, the orthopedic implant device is sterile packed using HAnano Surface technology. In another embodiment, the method further comprises a series of steps of subsequently laser melting thin metal layers to create complex geometries. In another embodiment, the method further comprises manufacturing using lost-wax casting, investment casting, or die casting with fillers. In another embodiment, the orthopedic implant device comprises titanium.

Various embodiments include a physical therapy and rehabilitation regimen for strengthening muscles and bones in a patient in need thereof, comprising providing to the patient an orthopedic implant device comprising a porous structure that approximates the shape of a bone, and has modulus of elasticity similar to that of said bone. In another embodiment, the muscle groups are related to injured, weak, or post-operative joints including associated ligaments and tissue.

Other embodiments include a method of manufacturing a prosthetic limb or part thereof using an additive manufacturing method comprising the steps providing a 3-dimensional model of the prosthetic limb or part thereof; inputting the 3-dimensional model to an additive manufacturing device; and using the additive manufacturing device to manufacture the prosthetic limb or part thereof.

Other features and advantages of the invention will become apparent from the following detailed description, taken in conjunction with the accompanying drawings, which illustrate, by way of example, various embodiments of the invention.

DESCRIPTION OF THE DRAWINGS

Exemplary embodiments are illustrated in referenced figures. It is intended that the embodiments and figures disclosed herein are to be considered illustrative rather than restrictive.

FIG. 28 illustrates that displacements for AM produced structures are similar.

DETAILED DESCRIPTION

Figure 1:
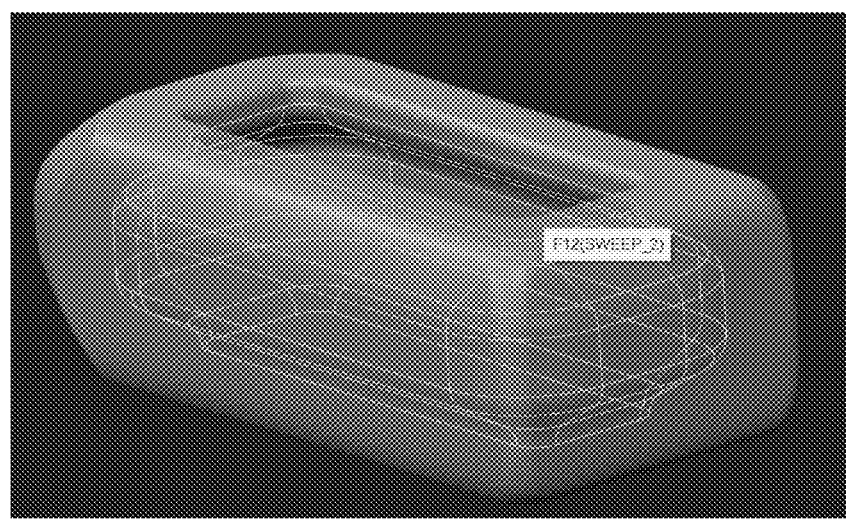
FIG. 1 illustrates one embodiment where material is removed internal to the interbody, thinning the walls for increased bone graft while preserving a wider endplate base to prevent subsidence.

All references, publications, and patents cited herein are incorporated by reference in their entirety as though they are fully set forth. Unless defined otherwise, technical and scientific terms used herein have the same meaning as commonly understood by one of ordinary skill in the art to which this invention belongs. Hornyak, et al., Introduction to Nanoscience and Nanotechnology, CRC Press (2008); Singleton et al., Dictionary of Microbiology and Molecular Biology 3rd ed., J. Wiley & Sons (New York, NY 2001); March, Advanced Organic Chemistry Reactions, Mechanisms and Structure 7th ed., J. Wiley & Sons (New York, NY 2013); and Sambrook and Russel, Molecular Cloning: A Laboratory Manual 4th ed., Cold Spring Harbor Laboratory Press (Cold Spring Harbor, N Y 2012), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

One skilled in the art will recognize many methods and materials similar or equivalent to those described herein, which could be used in the practice of the present invention. Indeed, the present invention is in no way limited to the methods and materials described.

Described herein is an orthopedic implant device, and methods of designing, manufacturing, implanting, and using the device. In one embodiment, disclosed herein are orthopedic implant devices comprising a porous structure, approximating the shape of a bone, and having modulus of elasticity similar to that of said bone. In some of these embodiments, the manufacturing of the orthopedic implant device comprises additive manufacturing technology.

As understood by someone skilled in the art, the term "additive manufacturing" or "AM" contemplates a manufacturing technology as defined in the international standard ASTM 2792-12. It refers to a process of making useful 3-dimensational objects through a series of sequential steps, forming the shape of the object one layer at a time. AM processes include, but are not limited to, three-dimensional printing (3DP) processes, laser-net-shape manufacturing, direct metal laser sintering (DMLS), direct metal laser melting (DMLM), plasma transferred arc, freeform fabrication, direct digital manufacturing, layered manufacturing, and rapid prototyping.

The AM method may be selected from, but is not limited to, stereolithography, mask stereolithography, mask projection stereolithography, polymer jetting, scanning laser sintering (SLS), scanning laser melting (SLM), electronic beam melting (EBM), and fused deposition modeling (FDM). AM technologies comprise processes which create objects by juxtaposition of volume elements according to a pre-determined arrangement that can be defined in a Computer Aided Design file (CAD). Such juxtaposition is the result of sequential operations such as building a material layer on top of a previously obtained material layer and/or juxtaposing a material volume element next to a previously obtained volume element.

As understood by one skilled in the art, the term "similar" or "similarity" contemplates having characteristics in common and/or closely resembling each other. Thus, the modulus of elasticity of an orthopedic implant device is similar to the modulus of elasticity of a bone if they are identical or if they are within 50% of each other, or more preferably within 20% of each other.

As understood by one skilled in the art, the terms "approximate," "approximates," or "approximating" the shape of a bone contemplates a shape that is close to the shape of the bone. In some embodiments, the shape may substantially exactly correspond to the shape of the bone. The term "substantially exactly" in this regard means that the shapes are exactly identical except for the eventual presence of tolerances that may result from making the device. In other embodiments, the shape is closely related to the shape of the bone, but not necessarily substantially exact.

In some embodiments, the porous structure of the orthopedic implant device has a porosity of 15% to 65%, more preferably porosity of 25-50%, and most preferably porosity of 25-35%. In some embodiments, the modulus of elasticity of the orthopedic implant device is less than 50 GPa. In some embodiments, the orthopedic implant device is made of titanium or titanium alloy.

In some embodiments, the porous structure of the orthopedic implant device is simple cubic, face centered cubic, body centered cubic, or hexagonal close packed structure. In some embodiments, the orthopedic implant device is an interbody fusion device. In some embodiments, the orthopedic implant device has a large surface contact area to the endplates to prevent linear subsidence while carrying a sufficiently large volume of bone graft area within the device to fuel the natural occurrence of a fusion. In some embodiments, the orthopedic implant device has large internal voids for bone graft.

In some embodiments, the cross sectional area of the orthopedic implant device as related to the thickness within the device is less than 90% of that of the endplates. In some of these embodiments, the thickness within the device is 25% to 50% of that of the endplates. In one embodiment, the thin walls enable increased bone graft.

In some embodiments, the orthopedic implant device has a variable entry angle, wherein the variable entry angle maximizes the contact surface area to the vertebral body, and wherein the entry angle is gradually decreased to offset the increasing insertion force. In some embodiments, the implant may be incorporated into expandable interbody cages, plates, screws, or other orthopedic devices benefitting from additive manufacturing In another embodiment, disclosed herein are methods of treating injuries or diseases affecting bones or muscles comprising (i) providing an orthopedic implant device, wherein the orthopedic implant device comprises a porous structure, approximates the shape of a bone, and has modulus of elasticity similar to that of bone, and (ii) using the orthopedic implant device to treat injuries and diseases affecting bones and muscles in a mammal. In some of these embodiments, the disease is osteoporosis, Paget's disease, osteogeneis imperfecta, bone cancer, rickets, osteomalacia, acromegaly, Perthes' disease, fibrous dysplasia, or oteromyelitis. In some embodiments, the mammal is human. In some embodiments, the mammal is an animal. In some embodiments, the treating comprises healing. In some embodiments, the treating comprises strengthening. In some embodiments, the treating comprises straightening.

In some embodiments, the orthopedic implant device is inserted adjacent to a bone structure. In some embodiments, the orthopedic implant device is inserted inside a bone structure. In some embodiments, the orthopedic implant device is an intervertebral interbody. In some of these embodiments, intervertebral interbody has a variable entry angle to first maximize the contact surface area to the vertebral body, and wherein the entry angle is gradually decreased to offset the increasing insertion force. In some embodiments, the implant device is inserted diagonally across the interbody space relative to the sagittal and coronal planes. In some embodiments, the orthopedic implant device couples two adjacent vertebrae. In some embodiments, the orthopedic implant device facilitates motion between the two adjacent vertebrae. In some embodiments, the implant is used to support or secure one or more bones.

In another embodiment, disclosed herein is a method of manufacturing an orthopedic implant device using an additive manufacturing method comprising the steps: (a) providing a 3-dimensional model of the orthopedic implant device; (b) inputting the 3-dimensional model to an additive manufacturing device; and (c) using the additive manufacturing device to manufacture the orthopedic implant device. In some of these embodiments, the orthopedic implant device comprises a porous structure that approximates the shape of a bone and has a modulus of elasticity similar to that of said bone. In some embodiments, the 3-dimensional model is created with computer aided design package, 3-dimensional scanner, or a digital camera and photogrammetry software.

In some embodiments, the porous structure has a porosity of 15% to 65%, or preferably a porosity of 25-35%. In some embodiments, the modulus of elasticity is less than 50 GPa. In some embodiments, the orthopedic implant device is made of titanium or titanium alloy. In some embodiments, the porous structure is simple cubic, face centered cubic, body centered cubic, or hexagonal close packed structure. In some embodiments, the orthopedic implant device is an interbody fusion device. In some embodiments, the orthopedic implant device has a large surface contact area to the endplates to prevent linear subsidence while carrying a sufficiently large volume of bone graft area within the device to fuel the natural occurrence of a fusion. In some embodiments, the orthopedic implant device has internal voids for bone graft. In one embodiment, the orthopedic implant device has a variable entry angle. In one embodiment, the variable entry angle maximizes the contact surface area to the vertebral body. In one embodiment, the entry angle is gradually decreased to offset the increasing insertion force. In some embodiments, the orthopedic implant device is incorporated into expandable interbody cages, plates, screws, or other orthopedic devices benefitting from additive manufacturing. In some embodiments, the orthopedic implant device is sterile packed using $HA^{nano}$ Surface technology.

In another embodiment, provided herein is a physical therapy and rehabilitation regimen for strengthening muscles and bones in a patient in need thereof, comprising providing to the patient an orthopedic implant device comprising a porous structure that approximates the shape of a bone, and has modulus of elasticity similar to that of said bone. In some of these embodiments, the muscle groups are related to injured, weak, or post-operative joints including associated ligaments and tissue.

In another embodiment, provided herein is a prosthetic limb or part thereof, comprising a porous structure that approximates the shape of a bone, and has modulus of elasticity similar to that of said bone.

In another embodiment, provided herein is a method of manufacturing a prosthetic limb or part thereof using an additive manufacturing method comprising the steps: (a) providing a 3-dimensional model of the prosthetic limb or part thereof; (b) inputting the 3-dimensional model to an additive manufacturing device; and (c) using the additive manufacturing device to manufacture the prosthetic limb or part thereof.

While some of the various devices, methods of treatment, and methods of manufacture described herein use the Additive Manufacturing technique, it will be appreciated by someone skilled in the art that any manufacturing technique, including the traditional manufacturing techniques, is suitable for making and using the devices disclosed herein. As well known to one of skill in the art, various embodiments described herein may be used or created by subsequently laser melting thin metal layers to create complex geometries, and the various methods and compositions described herein are in no way only limited to Additive Manufacturing techniques alone. Additional methodology may include, for example, lost-wax casting, investment casting, and die casting with fillers.

Embodiments of the present disclosure are further described in the following examples. The examples are merely illustrative and do not in any way limit the scope of the invention as claimed.

EXAMPLES

Example 1: Novel Improvement to Surface Contact Area

In some embodiments, the interbody device disclosed herein has a larger surface contact area to the endplates, thereby preventing linear subsidence while carrying a sufficiently large volume of bone graft area within the device to fuel the natural occurrence of a fusion. In some embodiments, contrary to a traditionally manufactured device, an AM manufacturing process allows the orthopedic device to create wide surface contact areas with many small dispersed voids creating large internal voids for bone graft. Endplate contact from the device to the bone preserves a lower contact stress by means of the smaller dispersed voids. In one embodiment, the orthopedic device disclosed herein is unique in having cells interconnected by smaller channels. Graft material (for example, autograft, allograft, synthetic, etc), packed into the device for fusion, travels within these interconnections, filling the larger cells. Once packed, the bone graft is entrapped within device to encourage bone healing and fusion. In one embodiment, the wall cross-sectional area as related to the thickness, within the device is less than 90% of that of the endplates, or preferably 25 to 50% as thin. In some embodiments, the thickness is about 5% of that of the endplates.

FIG. 1 illustrates that to prevent subsidence, material is removed internal to the interbody, the walls are thinned for increased bone graft, and the wider endplate is preserved.

Example 2: Novel Variable Section Radii Along Endplate Contact Surfaces

Figure 2:
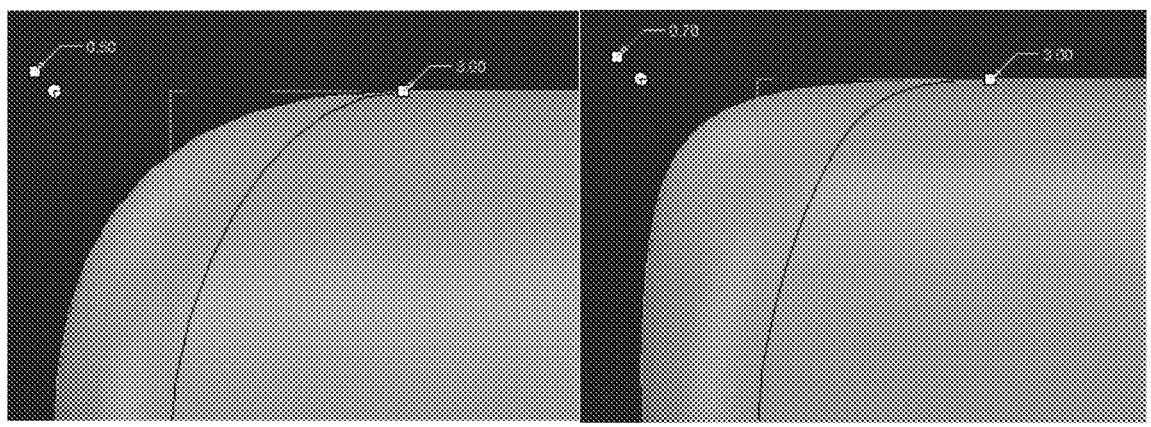
FIG. 2 illustrates that a gradually tightening arc, produced using Additive Manufacturing (AM), initially tangent to the endplate(s), allows for the widest useful footprint while resisting increasing eccentric loads.

In one embodiment, disclosed herein is an orthopedic implant device with a novel edge geometry comprising a variable radii. In some embodiments, this orthopedic implant device is manufactured using AM. As disclosed in FIG. 2, a gradually tightening arc, initially tangent to the endplate(s) allows for the widest useful footprint while resisting increasing eccentric loads. The novel edge geometry disclosed herein influences stress concentrations from the fusion device to the vertebral endplates, particularly during eccentric loading. This prevents subsidence via eccentric edge loading and straight axial compression. In FIG. 2, the radius is shown tangent to endplate as well as the side of the device. In one embodiment, the tangency to the endplate is critical to prevent subsidence.

Example 3: Novel Device Entry Angles

Figure 3:
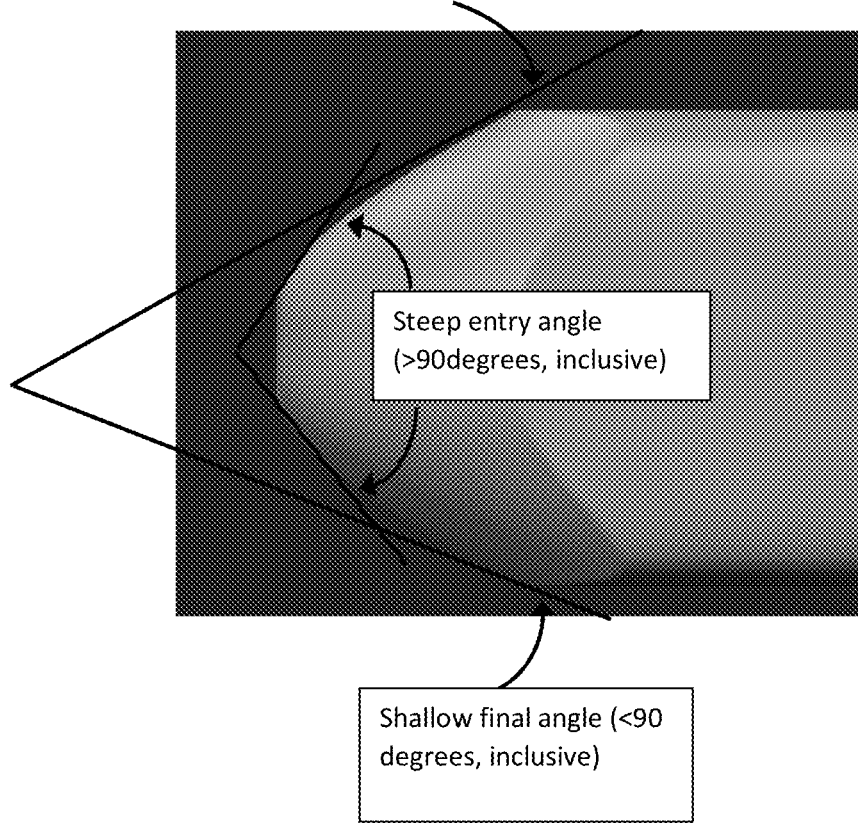
FIG. 3 illustrates that a variable insertion angle, produced using AM, will gradually decrease the force required to insert the interbody while distracting the interbody space, while maximizing the endplate surface area.

A steep device entry angles (>90 deg for example) would disrupt the least amount of endplate surface area and preserve a higher amount of endplate contact surface area as compared to a shallow entry angle. However, a steep angle increases the force required to insert the device, as it is less of a wedge. Adjacent intervertebral soft tissues are nonlinear visco-elastic; they become less pliable and more difficult to stretch with increasing strain. Therefore, the required insertion force will increase with the required increased distraction as the implant is inserted. In one embodiment, as disclosed in FIG. 3, the interbody disclosed herein has a variable entry angle to maximize the contact surface area to the vertebral body and to offer a gradually decreasing angle to offset the increasing insertion force. Thus, as the interbody is inserted, its distraction force increases with height. In some embodiments, a variable insertion angle is manufactured using AM. This variable insertion angle decreases the force required to insert the interbody while maximizing the endplate surface area.

Example 4: Novel Artistic Features

Figure 4:
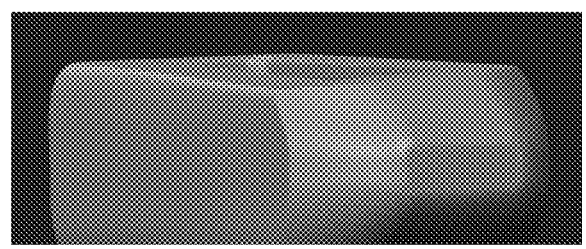
FIG. 4 illustrates that a variable endplate surface yields teeth and surface geometries that are difficult to produce by common means, is possible with AM.

In one embodiment, disclosed herein is a novel oblique lordosis on a straight Transforaminal Lumbar Interbody Fusion (TLIF). In some of these embodiments, the device is manufactured using AM. In one embodiment, the use of AM allows for the ease and cost effective manufacturing of the device. The device is inserted diagonally across the interbody space relative to the sagittal and coronal planes. In one embodiment, the lordosis is not in-line with any axis of the device and resides at a matching oblique angle. FIG. 4 is an illustration of a variable endplate surface yielding teeth and surface geometries that are difficult to produce by common means, now possible with AM.

Example 5: Bone Mass Communication Pathways

For a fusion to occur between the adjacent intervertebral devices, a sufficient bone fusion mass must be able to communicate between the endplates. For this to occur, the mechanical device must limit its surface contact. While thinner walls are preferred to maximize the fusion channels, this may result in an increased rate of subsidence. A porous structure will maximize the fusion channels. However, too porous of a web with reduced beams will result in heightened contact stresses while too small of a porous webbed structure will result in diminished bone fusion contact. In one embodiment, disclosed herein is a porous orthopedic implant device with porosity between 15% and 65% that does not result in heightened contact stresses, while providing enough porosity for bone fusion contact.

As one example, for illustrative purposes only, if the vertebrae bone endplate has an approximate modulus of 10 GPa, and the stress/modulus bone creep failure at about 3 hours is 0.006, then the maximum stress the bone should see is $=0.006*10$ GPa$=60$ MPa. Assuming a force of 5 KN, the required surface area is 5 KN/60,000 KPa$=8.3c$-5 $m^2=83$ $mm^2$. A 4 mm endplate wall thickness within a 25 mm$\times$20 mm anterior lumbar interbody fusion (ALIF) has a surface area of $(25*20-17*12)=296$ $mm^2$. In one embodiment, disclosed herein is an orthopedic device that, under these loading conditions, should not have a porosity that is approximately $(83/296*100\%)=28\%$. In one embodiment, the disclosure herein teaches a porosity of 15%-65%, preferably 25%-50%, and most preferably 25-35%.

In one embodiment, the porosity distribution of the device is 70/30, preferably 60/40, and most preferably 55/45. As an illustrative example, a 28% porous endplate contact surface where all of the material is surrounding a single pore will result in a large distance of unsupported bone, increasing the likelihood of subsidence. A porosity distribution of at least 70/30, preferably 60/40, and most preferable at least 55/45 avoids this likelihood of subsidence.

In one embodiment, the porosity is evenly distributed throughout the orthodontic implant device. As an illustrative example, a device with a high porosity on one feature or edge and a low porosity on another feature or edge may present a total porosity distribution of 50/50, yet behave in an uneven manner with different device stiffness on the respective features. This will stress shield the overall device leading to unnecessary subsidence by failing to evenly distribute the porosity. A fairly evenly distributed porosity avoids this concern.

Example 6: Novel Bulk Material vs. Device "Elastic Modulus"

Figure 5:
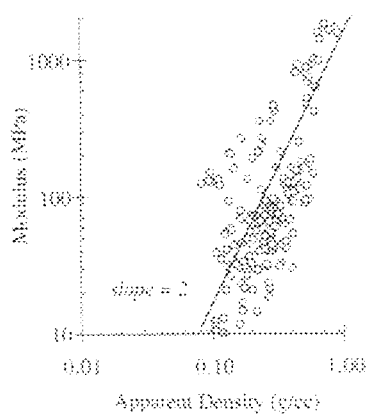
FIG. 5 illustrates experimentally recorded bone modulus verses apparent density, as is known in the art.

Trabecular bone mechanical properties are sensitive to apparent density. For example, the modulus of elasticity. E, in any loading direction is related to its apparent density, d, by a power-law relationship of the form: $E=a+b\cdot d^c$, where a, b, and c are constants. FIG. 5 illustrates an example plot, where experimentally recorded modulus, E, is plotted against apparent density, d.

Figure 6:
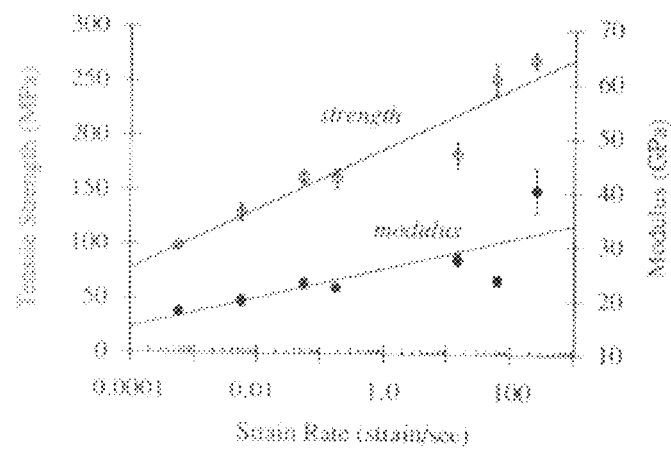
FIG. 6 illustrates experimentally recorded bone tensile strength and modulus to strain rates.

This relationship continues for cortical bone. The modulus for cortical bone varies between 10-40 GPa. Bone that has undergone more strain or activity, therefore becoming more dense, yields the highest modulus. FIG. 6 illustrates experimentally recorded tensile strength and modulus against strain rates.

In assuming a cancellous bone E of 0.45 GPa and a Cortical Bone E of 15 GPa, one can see why Polyetheretherketone (PEEK) implants, with an E of 3.5 GPa, may insight a more appropriate healing response to bone versus titanium with an E of 120 GPa. However, bone is not solid like PEEK; it is porous. Decreasing the porosity of bone increases its modulus of elasticity. Conversely, increasing the porosity of titanium lowers the bulk elastic modulus closer to that of bone.

Figure 7:
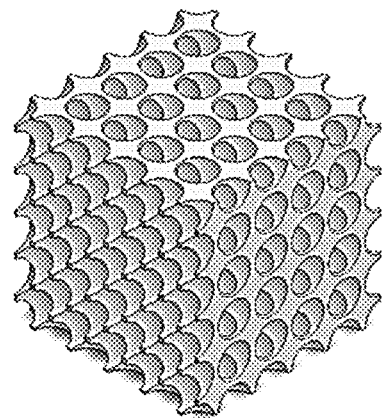
FIG. 7 illustrates porous titanium approximating the shape and device modulus of elasticity to that of bone.

In one embodiment disclosed herein are porous titanium orthopedic implants that are manufactured using AM. In other embodiments, porous titanium orthopedic implants are manufactured using traditional manufacturing. FIG. 7 illustrates one embodiment of a porous titanium orthopedic implant approximating the shape and modulus of elasticity to that of bone.

Figure 8:
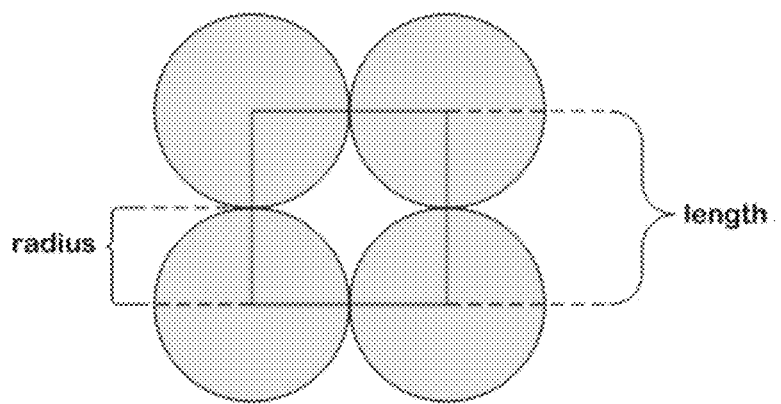
FIG. 8 illustrates a simple cubic structure.

In one embodiment, the orthopedic implants has structures that are simple cubic, face centered cubic, body centered cubic, or hexagonal close packed structure, or any combination thereof. In one embodiment, each of these different types of structures yield a variety of shapes and performance specifications. In one embodiment, FIG. 8 demonstrates a traditional cubic structure illustrating that the length between the spheres is at least twice the radius of the spheres.

Figure 9:
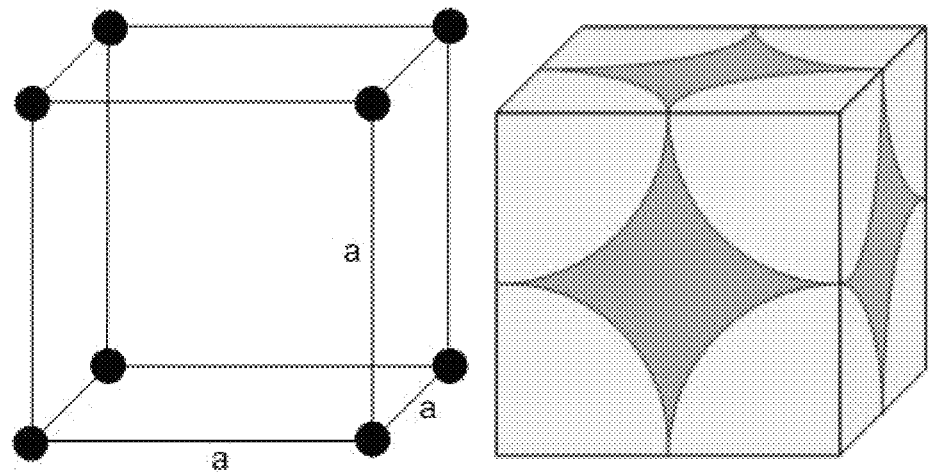
FIG. 9 illustrates simple cubic structures-schematic (left), and non-overlapping 3-D view (right).
Figure 10:
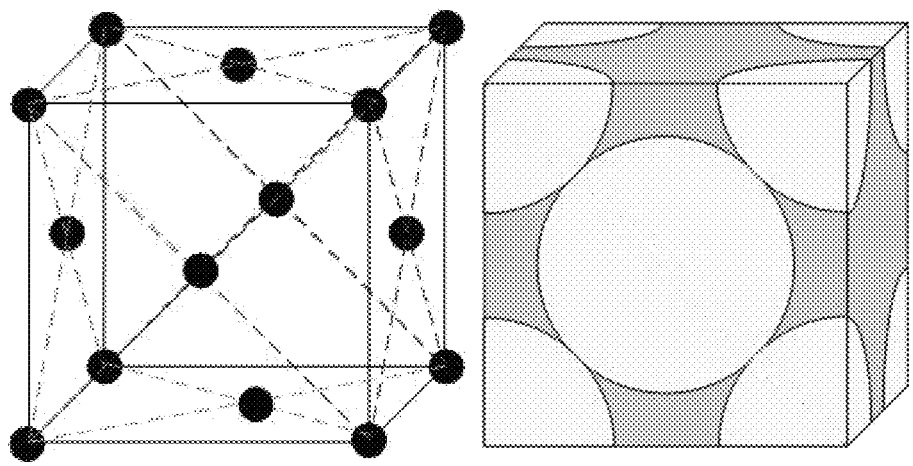
FIG. 10 illustrates faced centered structure-schematic (left), non-overlapping 3-D view (right).
Figure 11:
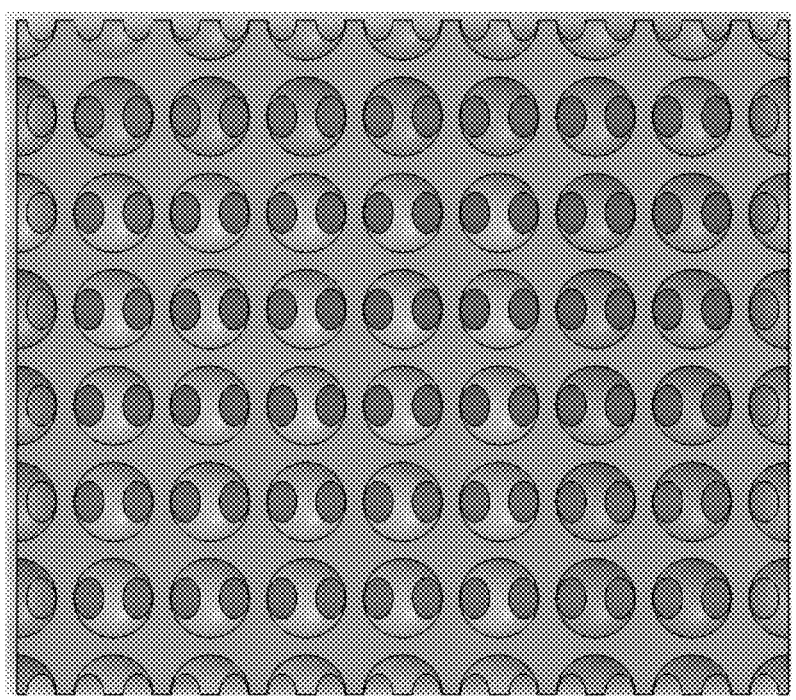
FIG. 11 illustrates a top view of an overlapping face centered cubic with the top center sphere suppressed.
Figure 12:
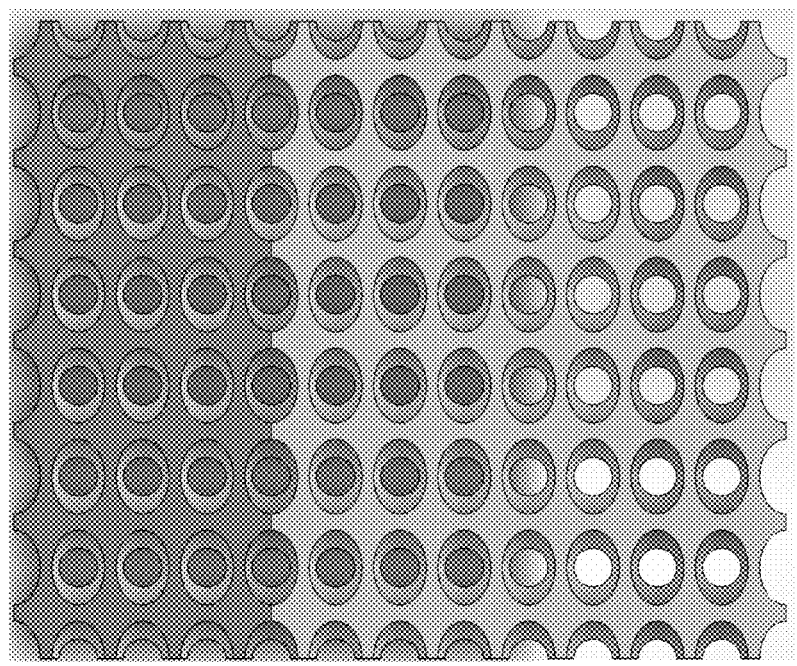
FIG. 12 illustrates an example of a 45° isometric view of an overlapping face centered cubic demonstrating porosity.

In another embodiment, the length is less than twice the radius, such that the spheres are overlapping. Overlapping spheres are critical to additive manufacturing cleaning and processing steps as well as to allow for true interconnected bone fusion pathways. Examples of different structures, and their impact on the modulus of elasticity, E, are illustrated in FIGS. 9-17. FIG. 9 illustrates a simple cubic structure: schematic (left), non-overlapping 3-D view (right). FIG. 10 illustrates a faced centered structure: schematic (left), non-overlapping 3-D view (right). FIG. 11 illustrates a top view of an overlapping face centered cubic with the top center sphere suppressed as described herein. FIG. 12 illustrates a 45° isometric view of an overlapping face centered cubic demonstrating porosity.

Example 7: Calculation of Modulus of Elasticity (E) Porosity of a Titanium Orthopedic Implant The porosity of a titanium orthopedic implant with an overlapping face centered cubic structure is calculated as illustrated herein. A 10×10×10 mm³ cube, with 200 N Force, and 1.75 Dia spheres separated at 2 mm yields 0.0007 mm displacement.

Calculating E using the equation, $$E = \frac{\text{tensile stress}}{\text{extensional strain}} = \frac{\sigma}{\varepsilon} = \frac{F/Ao}{\Delta L/Lo} = \frac{FLo}{Ao\Delta L}$$

where:
E is the Young's modulus (modulus of elasticity)
F is the force exerted on an object under tension;
$A_0$ is the original cross-sectional area through which the force is applied;
$\Delta L$ is the amount by which the length of the object changes;
$L_0$ is the original length of the object.
yields E=200N*10 mm/((10 mm*10 mm)*0.0007 mm)=28,571 N/mm²=28 Gpa.

In this illustrative example, based on this calculation, the titanium structure has a modulus of elasticity that is in the range of cortical bone.

Figure 13:
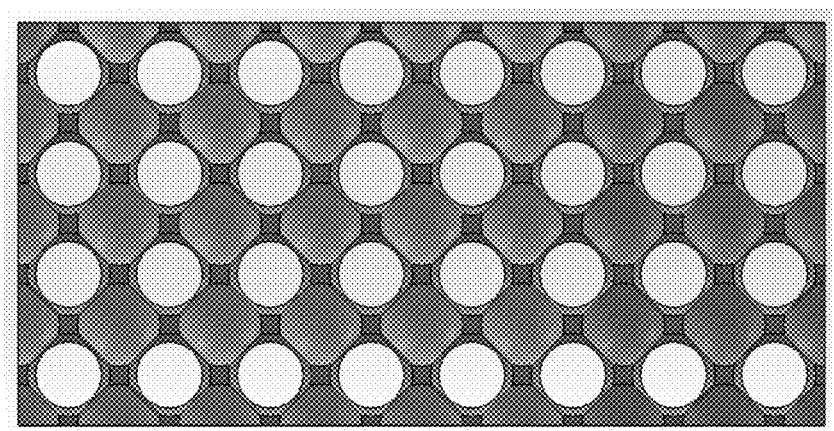
FIG. 13 illustrates an example of faced centered cubic with extra centered cubic spheres to produce front facing through channels.
Figure 14:
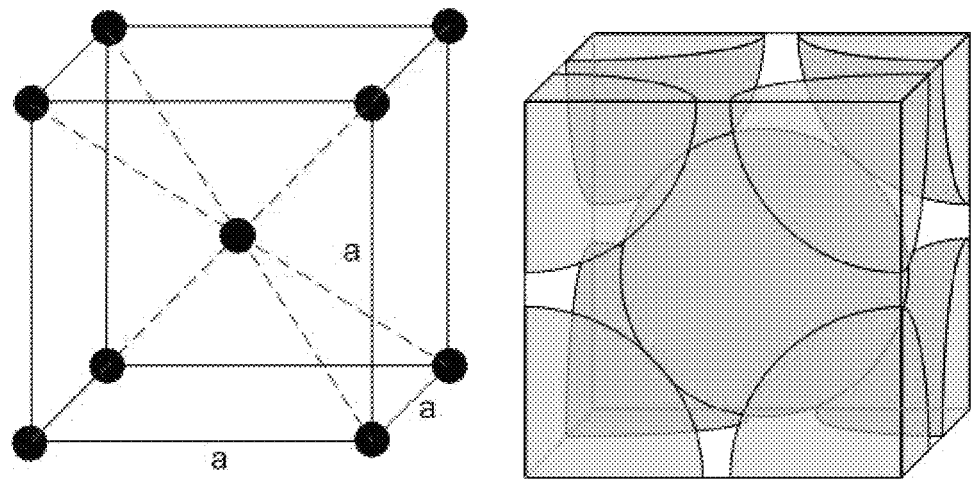
FIG. 14 illustrates a body-centered structure-schematic (left), non-overlapping 3-D view (right).
Figure 15:
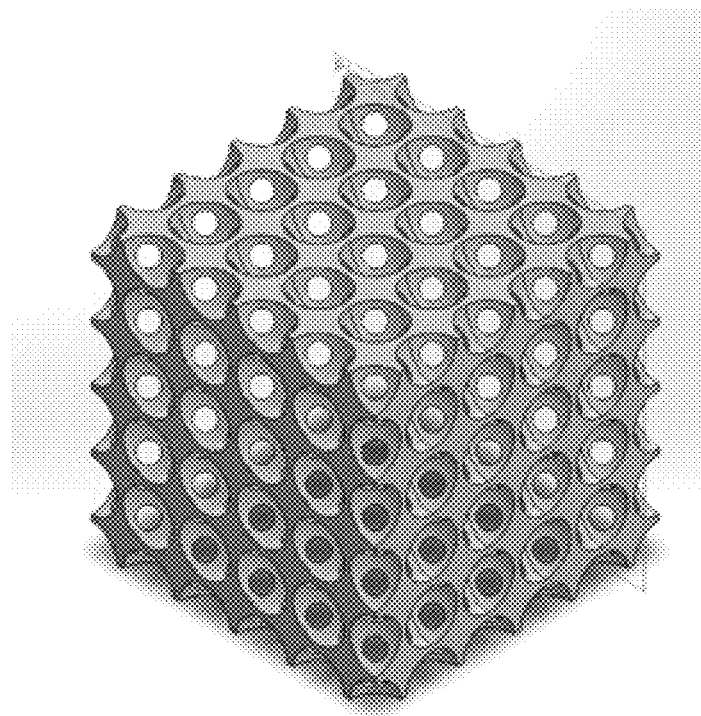
FIG. 15 illustrates an isometric view of an overlapping body centered cubic structure.
Figure 16:
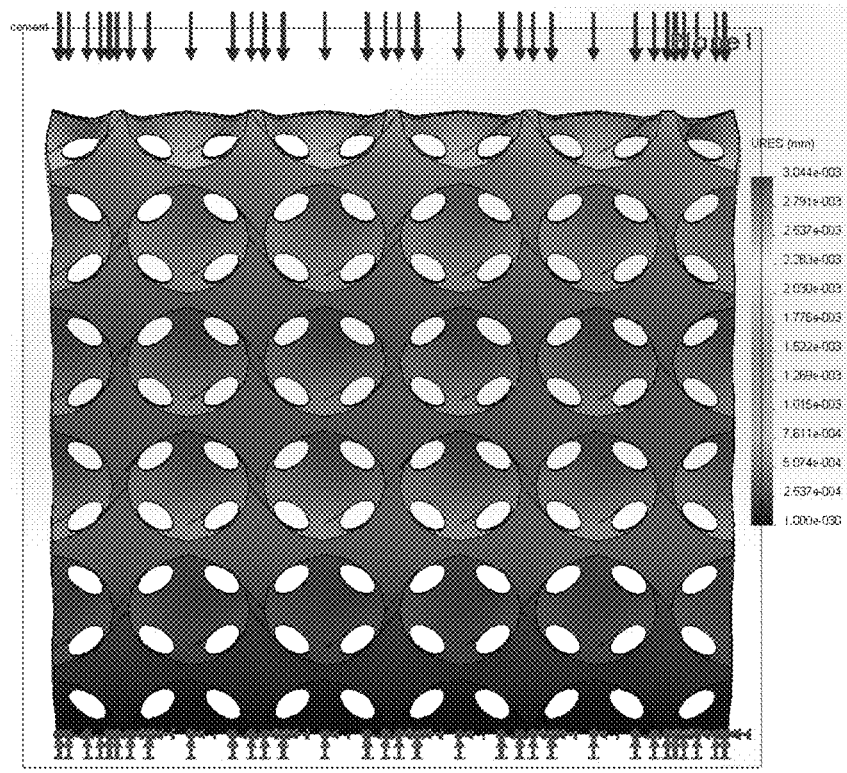
FIG. 16 illustrates the results of Finite Element Analysis (FEA).

FIG. 13 illustrates a faced centered cubic option with extra centered cubic spheres to produce front facing through channels. FIG. 14 illustrates a body centered cubic structure: schematic (left), non-overlapping 3-D view (right). FIG. 15 demonstrates an isometric view of an overlapping body centered cubic structure. As illustrated in FIG. 16 the Finite Element Analysis (FEA) results indicate displacement of 2.3e-3 mm. The new modulus of elasticity is: E=200N*10 mm/((10 mm*10 mm) 0.0023 mm)=28,571 N/mm²=8.6 GPa. This E is now less than cortical bone averages and yet still above cancellous, similar to that of PEEK.

Figure 17:
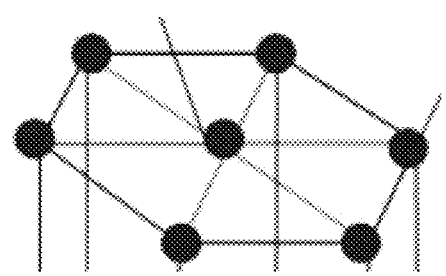
FIG. 17 illustrates hexagonal close packed structures.

FIG. 17 illustrates a hexagonal closed packed structure. The hexagonal closed pack offers additional performance benefits. As described and illustrated herein, with the advent of additive manufacturing, the material benefits of PEEK for interbody fusion applications have been decreased.

Example 8: Novel AM Sphere Shapes

When Additive Manufacturing incorporates a support material, complex shapes with overhanging geometry become capable. Although there are many dissolvable support materials, not all AM equipment with specific materials currently incorporate dissolvable materials. For these types of systems, supports must be mechanically removed, which is not a simple task for a complex porous structure. For these situations, porosity must be designed and orientated on the machine such that the internal porosity builds without support material.

Figure 18:
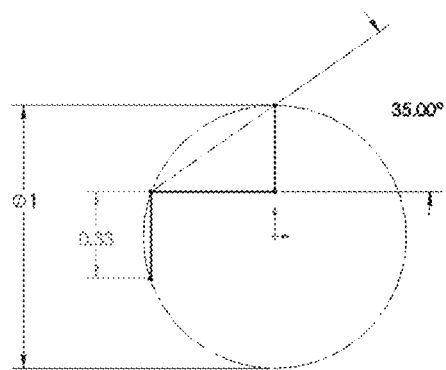
FIG. 18 illustrates Additive Manufacturing stepped geometry

This concept is illustrated in FIG. 18 by a 1 mm diameter sphere. If a maximum overhang angle of 35° is possible, the steps must be at least 0.33 mm in height and from both sides. This leaves a truncated circle, or sphere, that negates the design intent and stress/strain profile.

Figure 19:
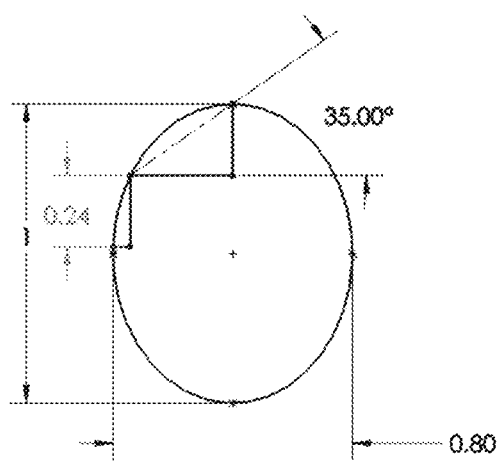
FIG. 19 illustrates that a reduced width from 1.0 mm to 0.8 mm reduces the step height to 0.24 from 0.33.
Figure 20:
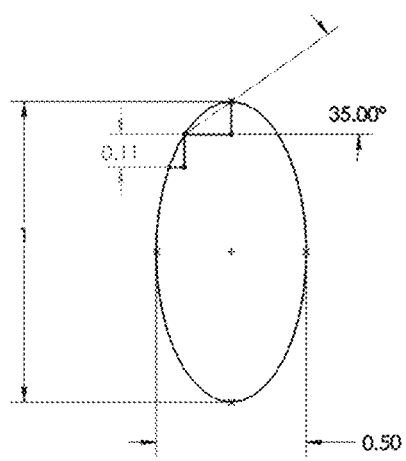
FIG. 20 illustrates a further reduction to 0.11 mm with a width of only 0.5 mm
Figure 21:
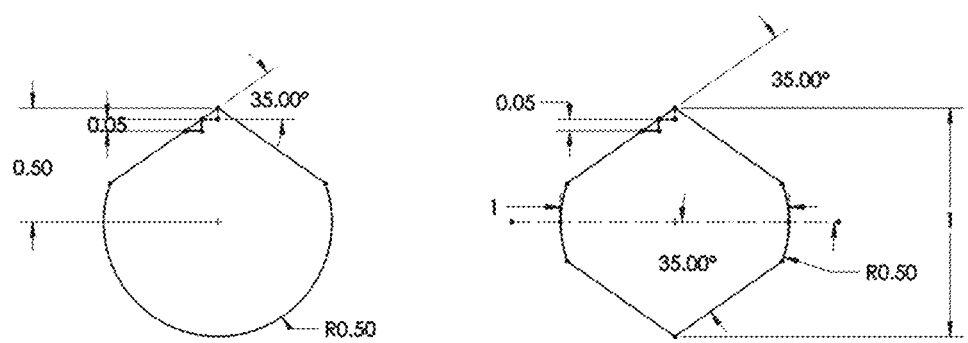
FIG. 21 illustrates that a teardrop or mirrored teardrop shaped feature for symmetry allows for the minimization of the build layer.

One possible solution disclosed herein is illustrated by the AM stepped-up geometry in FIG. 18. In one embodiment, described herein is an option is to design the spheres as oblong shapes, to preserve the integrity of the design intent. As illustrated in FIG. 19, a reduced width from 1 to 0.8 mm reduces the step height to 0.24 from 0.33. FIG. 20 illustrates further reduction to 0.11 mm with a width of only 0.5 mm. FIG. 21 illustrates that to allow for the minimization of the build layer, a tear drop shaped feature or a mirrored tear drop shape for symmetry are uniquely possible. Both of these tear drop shapes show upper geometry with a layer thickness of 0.05 mm.

Figure 30:
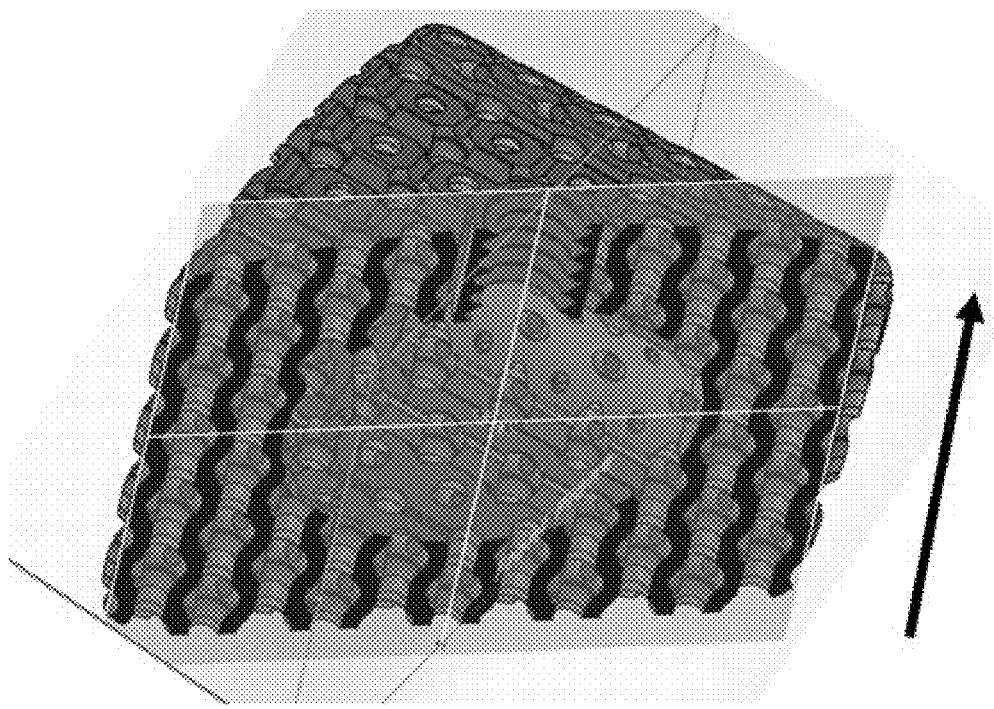
FIG. 30 illustrates one embodiment of the device incorporating interconnecting features orientated in the directing of the AM build, preventing material overhangs.

Another possible solution disclosed herein is to orientate the interconnecting channels parallel to the build direction. As illustrated in FIG. 30, there are no overhanging features as shown along the cross-sectional cut, allowing for an optimized AM build.

Figure 31:
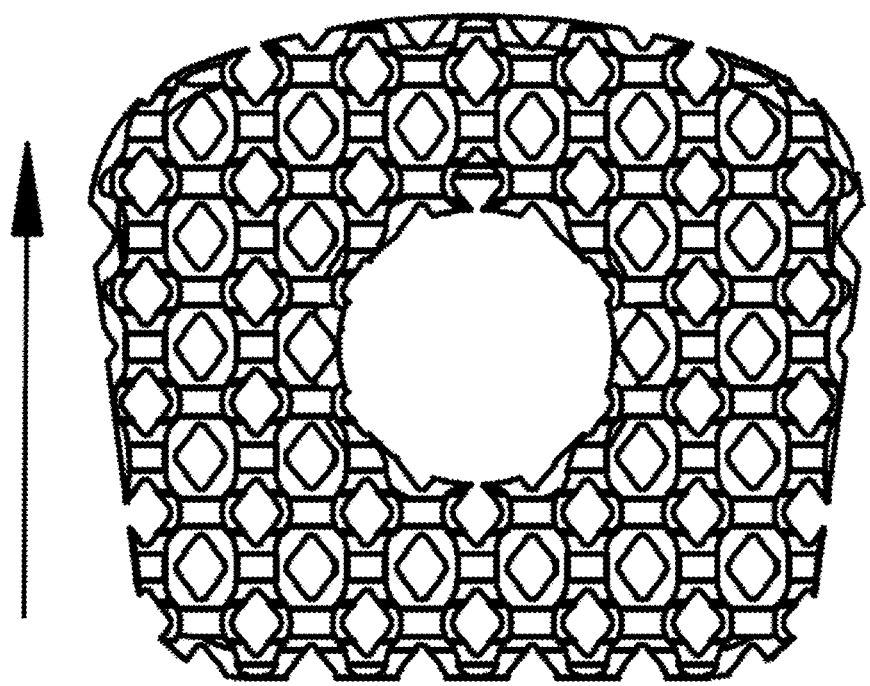
FIG. 31 illustrates one embodiment of the device incorporating interconnecting features orientated perpendicular to the direction of the AM build with narrow features and limited material overhangs.
Figure 32:
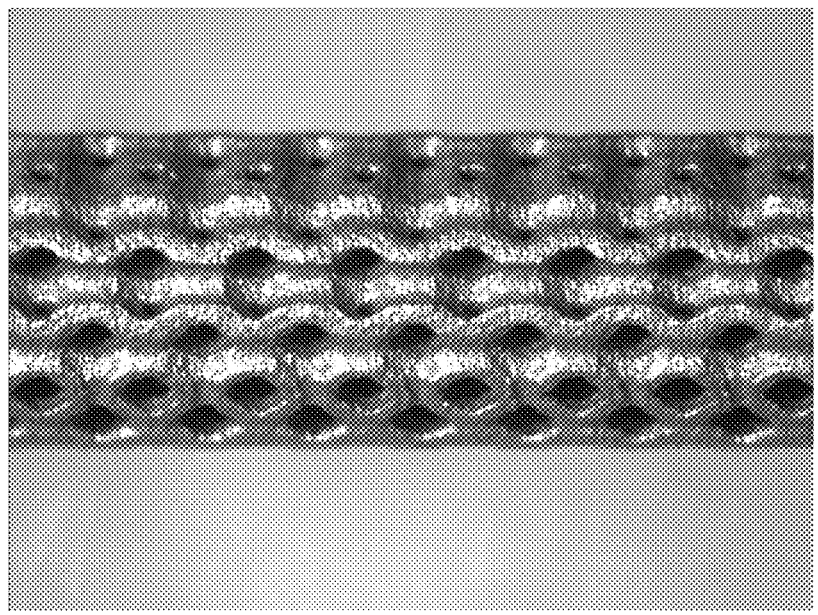
FIG. 32 illustrates, in accordance with embodiments herein, a 1× view of the structure as applied to a longer device as may be incorporated per a fracture pin such as a sacral iliac fixation pin.
Figure 33:
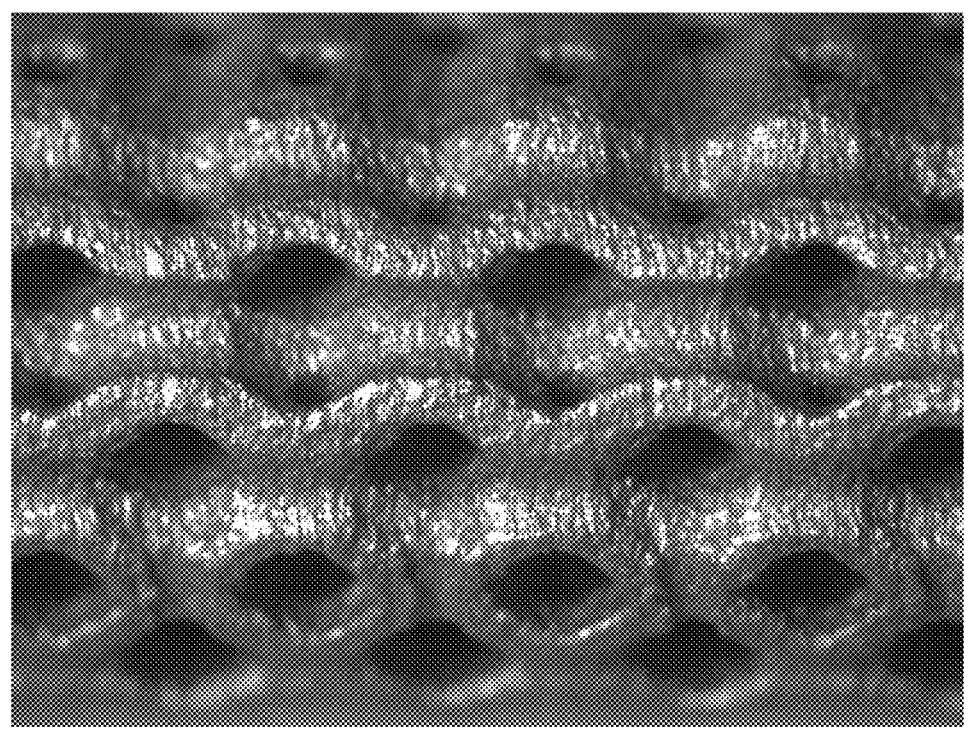
FIG. 33 illustrates, in accordance with embodiments herein, a magnified view clearly showing porous generally spherical structures with interconnections.
Figure 34:
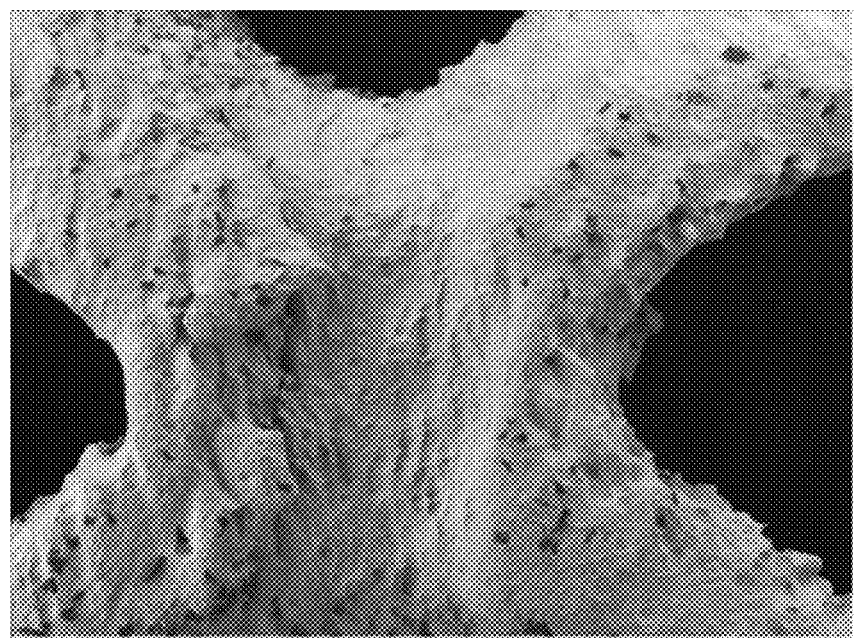
FIG. 34 illustrates, in accordance with embodiments herein, environmental scanning electron microscope (eSEM) image at 25× showing the structure of the formed interconnections.
Figure 35:
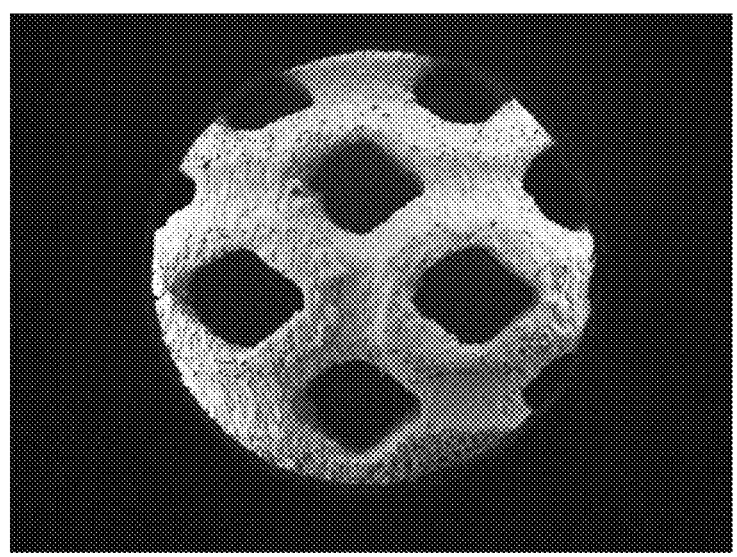
FIG. 35 illustrates, in accordance with embodiments herein, eSEM×100 showing the intricate surface topography required for bone cell attachment and formation.
Figure 36:
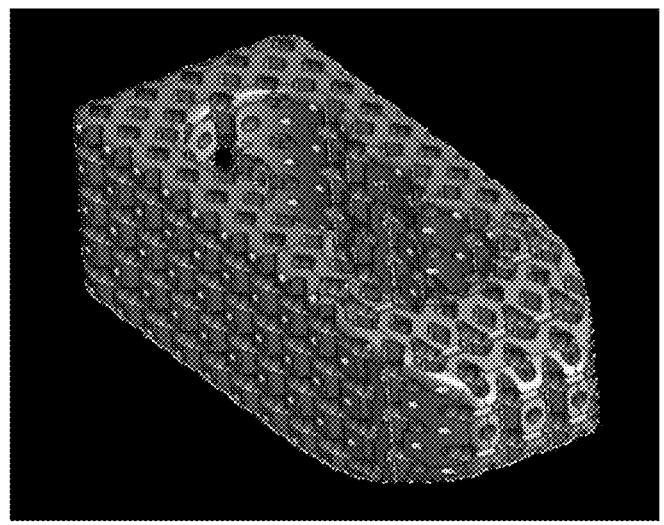
FIG. 36 illustrates, in accordance with embodiments herein, a posterior lateral interbody fusion cage.
Figure 37:
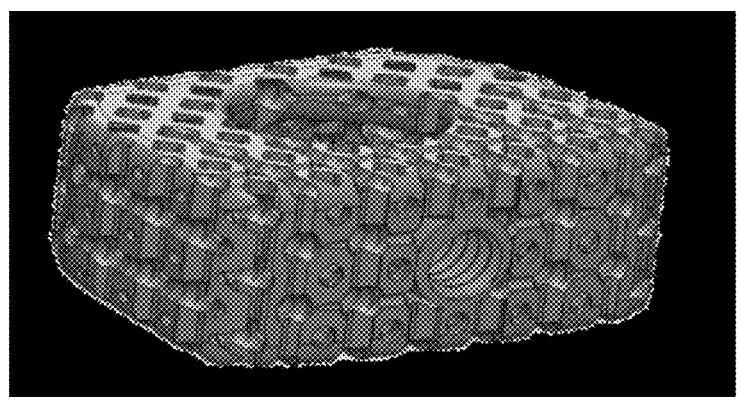
FIG. 37 illustrates, in accordance with embodiments herein, a cervical cage.
Figure 38:
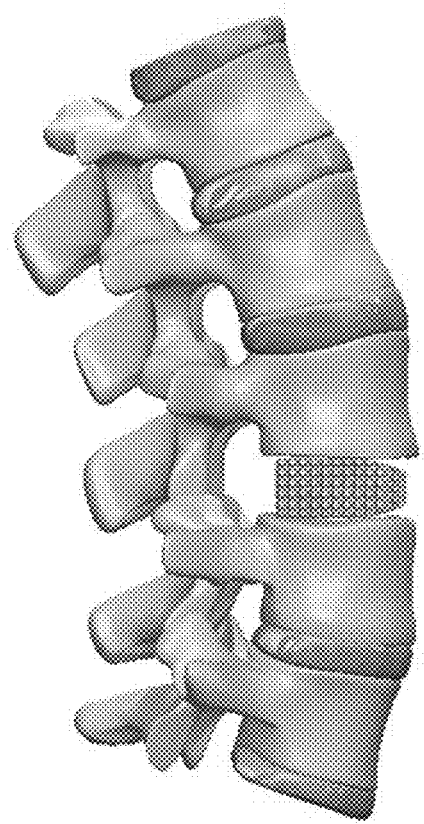
FIG. 38 illustrates, in accordance with embodiments herein, an example of the device used in a cervical and lumbar spine model.
Figure 39:
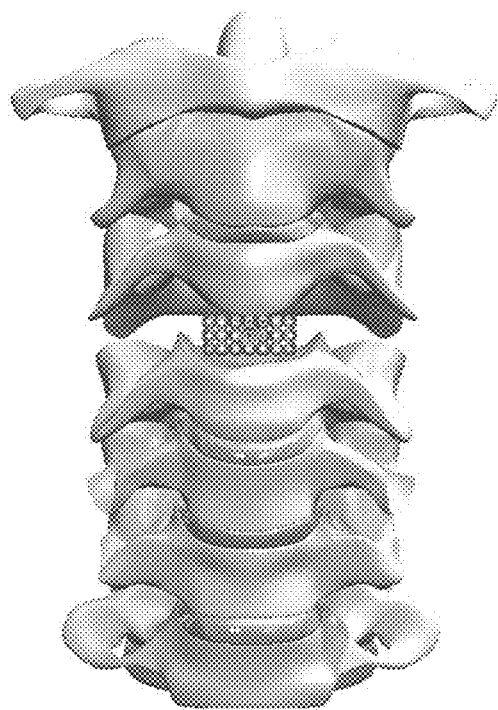
FIG. 39 illustrates, in accordance with embodiments herein, an example of the device used in a cervical and lumbar spine model.

Another possible solution disclosed herein is to orientate the interconnection channels perpendicular to the build direction, yet with narrow channels. As illustrated in FIG. 31, the material overhangs are greatly limited to allow for successful AM without limited supports.

Figure 22:
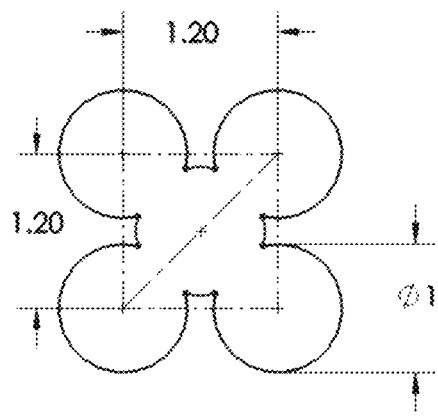
FIG. 22 illustrates a face centered cubic structure with a 1.0 mm diameter sphere is porous with a diagonal component length of less than 3R or 1.5 mm or with a length of 1.2 mm.
Figure 23:
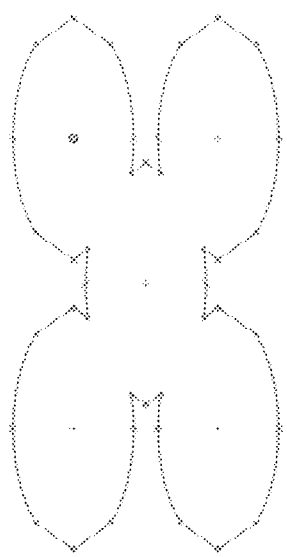
FIG. 23 illustrates that to achieve porosity, a double ellipse with symmetric teardrop shapes, the width of the cubic face center must be less than the height.
Figure 24:
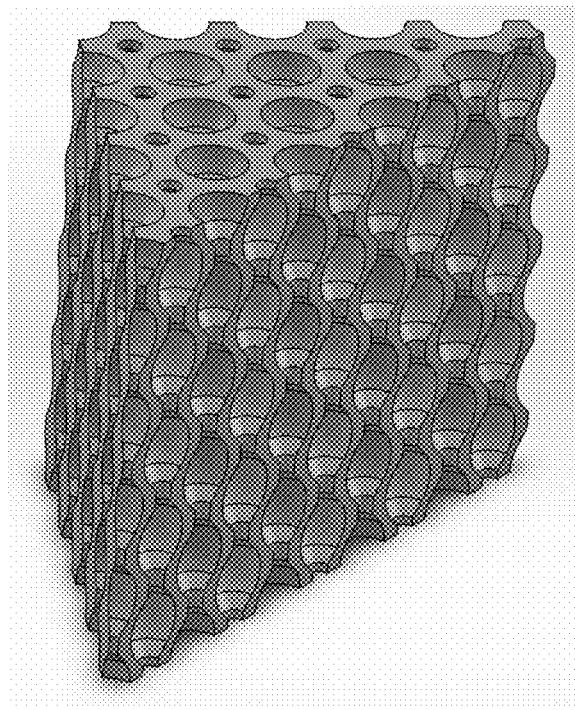
FIG. 24 illustrates a 3-dimensional view demonstrating the novel pattern, with a 45° degree cut plane.
Figure 25:
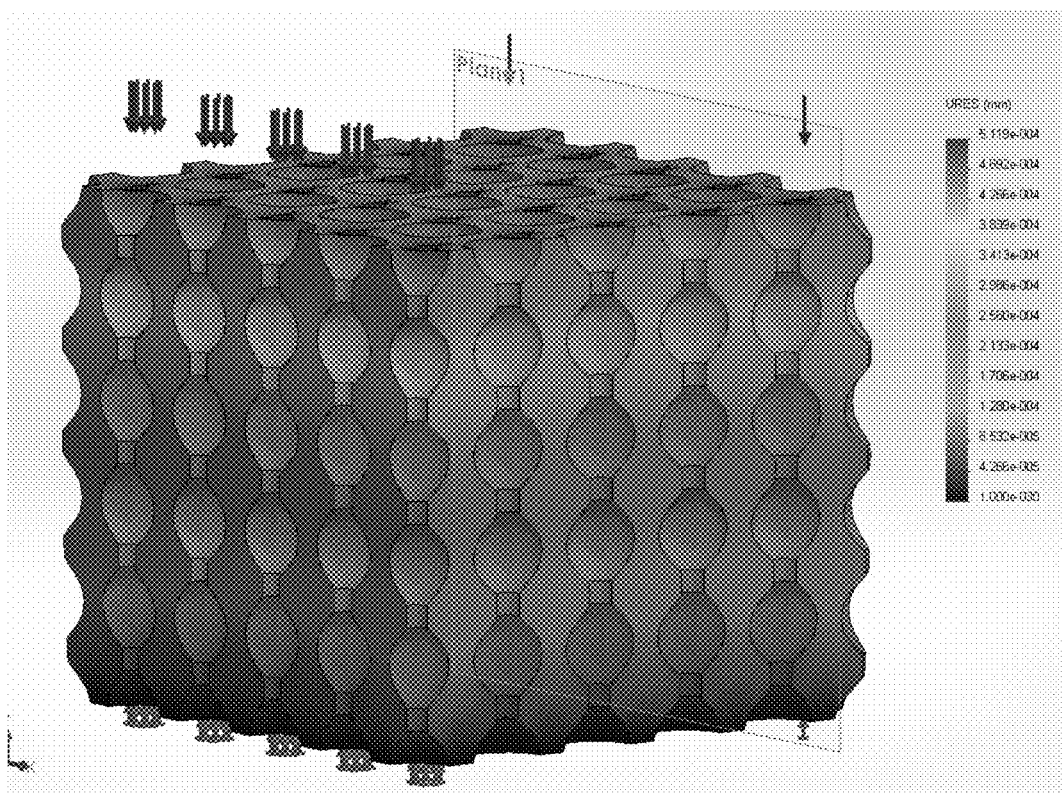
FIG. 25 illustrates displacements produced when spaced 2 mm apart in a body cubic formation.
Figure 26:
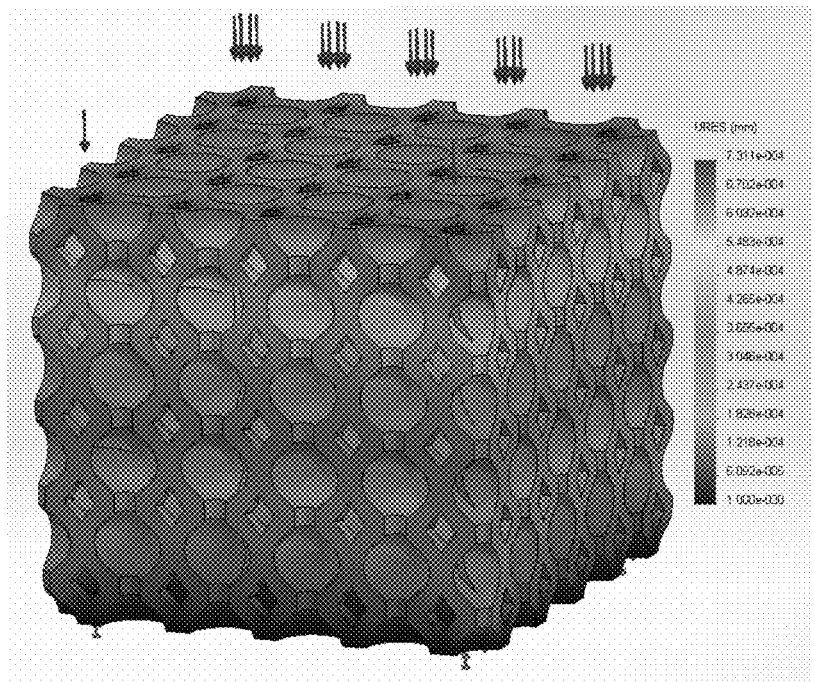
FIG. 26 illustrates that additional extrusions may be added within the spaces of the face centers to allow for additional strain per load.

In one embodiment, during and after the manufacturing of the orthopedic implant device, all internal corners are blended by the AM process. In some embodiments, the corners are rounded after AM using electropolishing or other means. In some embodiments, based on the shape of the orthopedic implant device, the layout of the cubic structure is altered such that the porosity remains unchanged. As one example, FIG. 22 illustrates that a face centered cubic structure with a 1 mm diameter sphere is porous with a diagonal component length of less than 3R or 1.5 mm or with a length of 1.2 mm. FIG. 23 illustrates that in order to achieve porosity, a double ellipse with symmetric tear drop shapes, the width of the cubic face center must be less than the height. FIG. 24 illustrates a 3-dimensional view of this novel pattern, with a 45 degree cut plane. FIG. 25 illustrates displacements produced when as spaced 2 mm apart in a body cubic formation: E=200N*10 mm/((10 mm*10 mm) 0.0005 mm)=40,000 N/mm$^2$=40 GPa. FIG. 26 illustrates that additional extrusions may be added within the spaces of the face centers to allow for additional strain per load.

Example 9: Positive Porous Spheres

Figure 27:
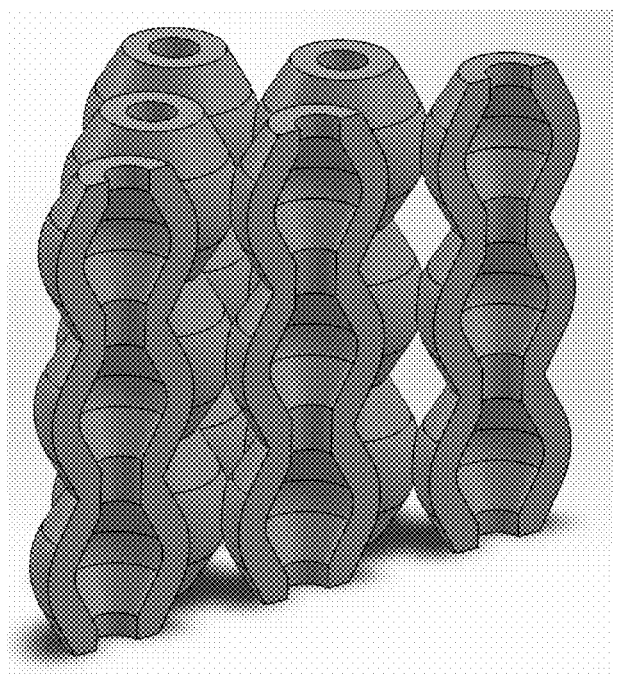
FIG. 27 illustrates AM produced porous structures.
Figure 28:
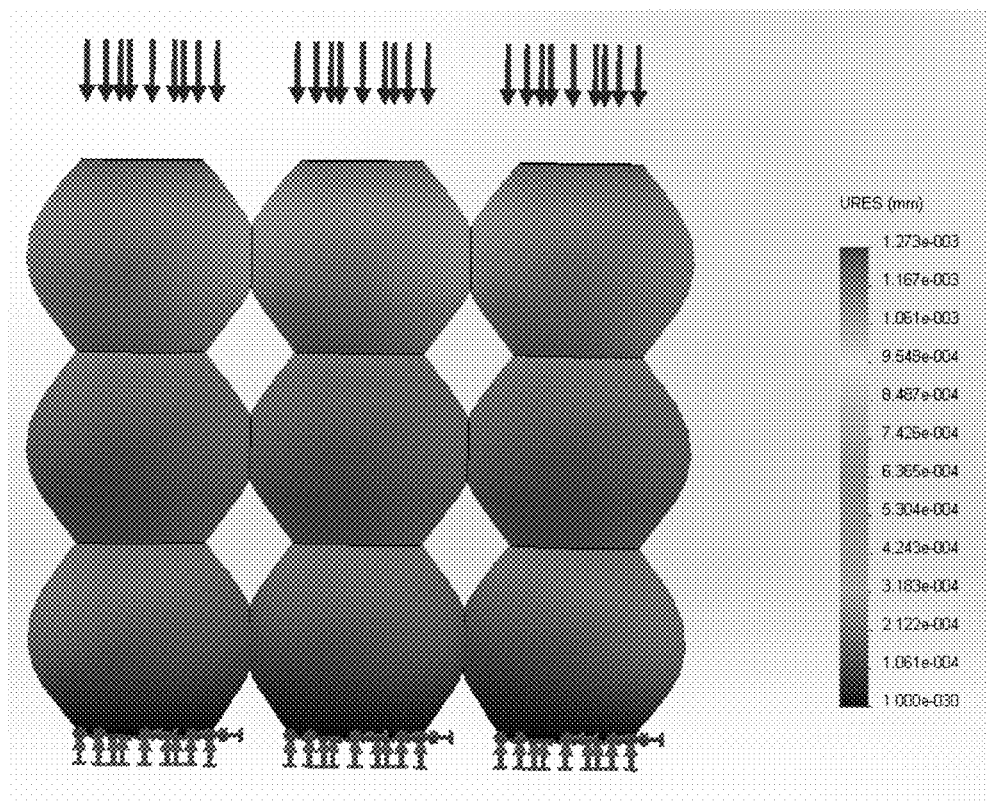

In one embodiment, as described herein, the spheres are enacted as cuts into the base material. In another embodiment, individually produced porous, appropriately shaped spherical structures are interlinked to manufacture the orthopedic implant device. FIG. 27 is an illustration of additively produced porous structures. FIG. 28 illustrates that displacements for such structures are similar: E=200N*6 mm/((6 mm*6 mm) 0.0013 mm)=25641 N/mm$^2$=25 GPa.

Example 10: Internal and External Surface Topography

Additive Manufacturing leaves a typically coarse surface topography as compared to traditional manufacturing (turning) methods. In some embodiments, for bone mechanical interlocking using on-growth, this presents an advantage for fusion devices. In other embodiments, the coarseness may adversely affect surrounding tissue and bone structures, particularly during insertion. In some embodiments, disclosed herein is a method to smooth these surfaces while preserving the internal surface topography by means of outer mechanical agitation such as tumbling. In some embodiments, the tumbling media is of sufficient size as to being unable to travel to all internal voids. In one embodiment, the preferred method is magnetic tumbling with spheres at least 101% the size of the device spheres and porosity, more preferably at least 150% or greater across the largest aspect relative to the titanium porous structure's largest aspect or diameters. In some embodiments, the aggressive tumbling has the added benefit of knocking any partially build and frail elements off the device.

Example 11: Surface Enhancements and Sterile Packaging

It is commonly known in the art that repeated cleaning and steam sterilization of medical devices within the bounds of hospital protocols result in foreign deposits, which reduces titanium's natural osteoconductive properties. Further, HA$^{nano}$ Surface and HA$^{micro}$ Surface treatments (www.promimic.com), which yield faster bone on-growth, cannot be steam sterilized.

In one embodiment, disclosed herein is a HA$^{nano}$ Surface and HA$^{micro}$ Surface sterile packed orthopedic implant device. In some embodiments, the orthopedic implant device is an additive manufactured device. A preservation of the porosity is important compared to a 100% packing the porosity with a bone preferentially material as any such material must be absorbed for the natural bone fusion to present within the porosity.

Figure 29:
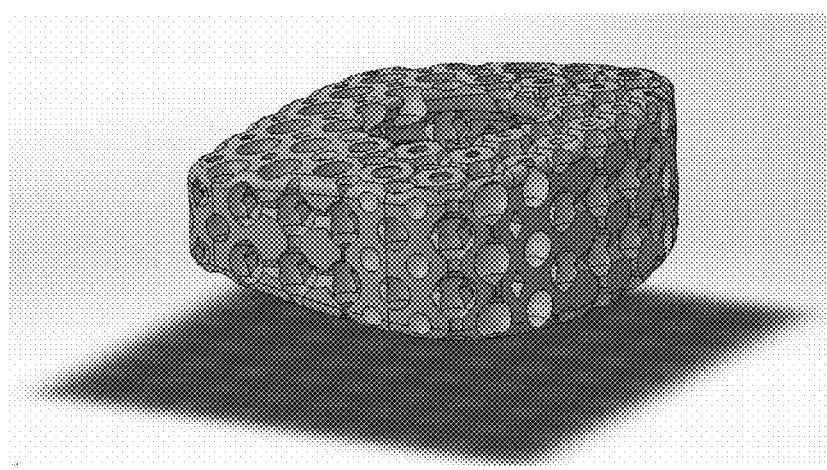
FIG. 29 illustrates one embodiment of the device incorporated into a preferred interbody fusion device.

In these embodiments, the surface treatment fills within the porosity a layer thickness reducing no less than 20% of the previous porosity. More specifically, the surface treatment only adds about 20 nm of surface thickness within all surfaces of the orthopedic implant device. This 20 nm layer accelerates the osteointegration with an osteoconductive surface. By further increasing the bone-like chemistry, this unique method allows for regulatory clearance of a bone fusion device without supplemental autograph or allograft. In a preferred embodiment, the surface material is hydroxyapatite. In some of these embodiments, hydroxyapatite is present as a crystalline structure. FIG. 29 illustrates some of the features of the interbody fusion device as disclosed herein. In some embodiments, the designs disclosed herein are incorporated into expandable interbody cages, plates, screws, or other orthopedic devices benefiting from additive manufacturing.

Throughout this disclosure, suitable materials for making the orthopedic implant includes metals and metal alloys including CoCrMo, CoCr, titanium alloys, commercially pure Ti (cpTi), medical grade stainless steels, tantalum, tantalum alloys, and Nitinol ("NiTi"). In a preferred embodiment, the implant is manufactured from titanium.

Example 12: Device Void Filling Method

Filling the device with bone graft material aids the natural occurrence of a fusion by providing the required building materials for fusion. Traditional packing of cages typically involves finger pressing graft material into the center of the device. The device void filling method disclosed herein fills any larger openings. In one embodiment, additional kneading is required to fill the smaller voids. In another embodiment, suction is used to fill the voids. By pulling a vacuum around the device, bone graft fills the voids. The bone graft is contained within the filling space by means of a micro filter, by where the vacuum is pulled, yet the graft material is unable to leave the space, allowing for distribution within the cage. As the space is compressed, the air and any added liquid or blood is able to evacuate, forcing the graft material into the cage.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a," "an," and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

What is claimed is:

1. A method of treatment, comprising:
   a. relative to a mammal, positioning an orthopedic device comprising a porous structure comprising a cross-section with pores aligned and interconnected such that centers of adjacent pores are aligned along a linear arrangement defining a straight path through the orthopedic device; and
   b. treating a disease or injury by implanting the orthopedic device in the mammal.

2. The method of claim 1, wherein the orthopedic device comprises an intervertebral interbody implant and positioning the orthopedic device comprises inserting the orthopedic device between vertebrae.

3. The method of claim 2, wherein the orthopedic device is inserted to abut a surface of each of the vertebrae.

4. The method of claim 3, wherein the orthopedic device comprises a height dimension perpendicular to the surface of each of the vertebrae, and a width dimension parallel to the surface of each of the vertebrae, the height dimension is greater than the width dimension, and implanting the orthopedic device comprises orienting the pores to have sidewalls of the pores that correspond to the height dimension substantially perpendicular to the abutting surfaces.

5. The method of claim 1, wherein each pore of the aligned and interconnected pores comprise a tear drop shape.

6. The method of claim 1, wherein the cross-section with aligned and interconnected pores comprises a repeating pattern of pores defined by non-linear, continuous sidewalls of material having a sinusoidal shape.

7. The method of claim 1, wherein the cross-section with aligned and interconnected pores comprises a repeating pattern of pores defined by continuous, sloping sidewalls of material, wherein each pore in the repeating pattern of pores comprises two opposing acute angles and two opposing obtuse angles.

8. The method of claim 1, wherein the orthopedic device comprises a first end plate and a second end plate, interconnecting walls that connect the first end plate to the second end plate at a plurality of edges, at least one of which defines a variable radius in a plane substantially perpendicular to the straight path, and wherein the porous structure is within a space between the first end plate and the second end plate the end plates and encompassed by the interconnected walls.

9. The method of claim 1, wherein the orthopedic device comprises an additively manufactured structure formed using a series of steps of subsequently laser melting thin metal layers to create complex geometries.

10. A method of manufacturing an orthopedic implant device, comprising:
   1. Inputting a 3-dimensional model to an additive manufacturing device; and
   2. Using the additive manufacturing device to manufacture the orthopedic implant device to have an internal void for bone graft material, opposing surfaces for contacting endplates, and one or more cross-sections with web-like pores and channels, the channels defined by non-linear sidewalls having a sinusoidal shape.

11. The method of claim 10, wherein the orthopedic implant device comprises a porous structure that approximates the shape of a bone and has a modulus of elasticity similar to that of said bone.

12. The method of claim 11, wherein the porous structure has a porosity of 25-35% and a modulus of elasticity is less than 50 GPa.

13. The method of claim 10, wherein the channels of the orthopedic implant device are substantially parallel to planes running through the opposing surfaces.

14. A method of treatment, comprising:
   a. relative to a mammal, positioning an additively manufactured orthopedic device comprising a porous structure comprising a cross-section along a plane parallel to a build direction of the orthopedic device, the cross-section having a repeating pattern of pores defined by continuous, sloping sidewalls of material, wherein each pore in the repeating pattern of pores comprises two opposing acute angles and two opposing obtuse angles; and
   b. treating a disease or injury by implanting the orthopedic device between bone surfaces in the mammal such that the plane is parallel to the bone surfaces.

15. The method of claim 14, wherein positioning the orthopedic device comprises inserting the orthopedic device into the mammal and orienting the orthopedic device relative to the mammal such that the two opposing acute angles point towards or away from leading and trailing ends of the orthopedic device.

16. The method of claim 10, wherein using the additive manufacturing device to manufacture the orthopedic implant device further comprises forming an edge geometry of a leading end of the orthopedic implant device to have variable radii.

17. A method of treatment, comprising:
   a. relative to a mammal, positioning an orthopedic device comprising two end plates a first end plate and a second end plate, interconnecting walls that connect the first end plate to the second end plate at a plurality of edges, at least one of which joins a generally planar segment of the first end plate to the interconnecting walls and defines a variable radius, and a porous structure within the end plates and the interconnecting walls; and
   b. treating a disease or injury by implanting the orthopedic device in a mammal with the first end plate against a first bone surface.

18. The method of claim 17, wherein positioning an orthopedic device comprises inserting a leading end of an intervertebral interbody implant relative to the mammal, the leading end having the at least one of the plurality of edges that defines the variable radius.

19. The method of claim 18, wherein upon inserting the leading end of the intervertebral interbody implant relative to the mammal, a first vertebral body abuts the first end plate and a second vertebral body abuts the second end plate.

20. The method of claim 10, wherein the web-like pores are oblong and using the additive manufacturing device to manufacture the orthopedic implant device to have one or more cross-sections with web-like pores and channels comprises orienting the web-like pores to reduce overhang between successive material layering processes.

21. The method of claim 10, wherein each of the web-like pores comprises a concave curved interior wall.

22. A method of treatment, comprising:
   a. relative to a mammal, positioning an orthopedic device comprising a porous structure comprising a cross-section with pores aligned and interconnected along a linear arrangement defining a straight channel with integrally-formed sidewalls through the orthopedic device; and
   b. treating a disease or injury by implanting the orthopedic device in the mammal.

23. The method of claim 22, wherein:
   the orthopedic device comprises an intervertebral interbody implant;
   positioning the orthopedic device comprises inserting the orthopedic device between vertebrae;
   the orthopedic device is inserted to abut a surface of each of the vertebrae;
   the orthopedic device comprises a height dimension perpendicular to the surface of each of the vertebrae, and a width dimension parallel to the surface of each of the vertebrae;
   the height dimension is greater than the width dimension; and
   inserting the orthopedic device comprises orienting the pores to have sidewalls of the pores that correspond to the height dimension substantially perpendicular to the abutting surfaces.

24. The method of claim 22, wherein each pore of the aligned and interconnected pores comprise a tear drop shape.

25. The method of claim 22, wherein the integrally-formed sidewalls have a sinusoidal shape.

26. The method of claim 22, wherein the cross-section with aligned and interconnected pores comprises a repeating pattern of pores defined by continuous, sloping sidewalls of material, wherein each pore in the repeating pattern of pores comprises two opposing acute angles and two opposing obtuse angles.

27. The method of claim 22, wherein the orthopedic device comprises a first end plate and a second end plate, interconnecting walls that connect the first end plate to the second end plate at a plurality of edges, at least one of which defines a variable radius in a plane substantially perpendicular to the straight channel, and wherein the porous structure is within a space between the first end plate and the second end plate and encompassed by the interconnected walls.

28. A method of treatment, comprising:
   a. relative to a mammal, positioning an additively manufactured orthopedic device fabricated along a build direction, the orthopedic device comprising a first end plate and a second end plate, both of which are parallel to the build direction, interconnecting walls that connect the first end plate to the second end plate at a plurality of edges, at least one of which joins the first end plate to the interconnecting walls and defines a variable radius, and a porous structure within a space defined between the first end plate and the second end plate and encompassed by the interconnecting walls; and b. treating a disease or injury by implanting the orthopedic device in a mammal with the first end plate against a first bone surface.

29. The method of claim 28, wherein positioning an orthopedic device comprises inserting a leading end of an intervertebral interbody implant relative to the mammal, the leading end having the at least one of the plurality of edges that defines the variable radius.

30. The method of claim 29, wherein upon inserting the leading end of the intervertebral interbody implant relative to the mammal, a first vertebral body abuts the first end plate and a second vertebral body abuts the second end plate.

31. A method of manufacturing an orthopedic implant device, comprising:
   1. Inputting a 3-dimensional model to an additive manufacturing device, the 3-dimensional model comprising:
      a first end plate shaped to abut a first vertebra;
      a second end plate shaped to abut a second vertebra; and
      interconnecting walls that connect the first end plate to the second end plate; and
   2. Using the additive manufacturing device to manufacture the orthopedic implant device along a build direction parallel to the first end plate and the second end plate, such that the orthopedic implant device comprises a plurality of interconnecting pores between the first end plate and the second end plate.

32. The method of claim 31, wherein manufacturing the orthopedic implant device comprises creating one or more cross-sections with web-like pores and channels.

33. The method of claim 32, wherein the channels of the orthopedic implant device are substantially parallel to planes running through the first end plate and the second end plate.

34. The method of claim 31, wherein the orthopedic implant device comprises a porous structure that approximates the shape of a bone and has a modulus of elasticity similar to that of said bone.

35. The method of claim 31, wherein the orthopedic implant device has a porosity of 25-35% and a modulus of elasticity is less than 50 GPa.

* * * * *